US010226179B2

(12) United States Patent
Maslowski et al.

(10) Patent No.: US 10,226,179 B2
(45) Date of Patent: Mar. 12, 2019

(54) METHOD, SYSTEM AND SOFTWARE PRODUCT FOR CREATING VARIABLE ENVIRONMENTS IN MEDICAL DIAGNOSTIC IMAGING ROOMS

(71) Applicant: PDC Facilities, Inc., Hartland, WI (US)

(72) Inventors: James P. Maslowski, Wauwatosa, WI (US); Elmer B. Woods, West Bend, WI (US); R. Michael Slemin, Ixonia, WI (US)

(73) Assignee: PDC Facilities, Inc., Hartland, WI (US)

( * ) Notice: Subject to any disclaimer, the term of this patent is extended or adjusted under 35 U.S.C. 154(b) by 750 days.

(21) Appl. No.: 13/851,556

(22) Filed: Mar. 27, 2013

(65) Prior Publication Data

US 2014/0121453 A1    May 1, 2014

Related U.S. Application Data

(60) Provisional application No. 61/616,194, filed on Mar. 27, 2012.

(51) Int. Cl.
| | |
|---|---|
| *A61B 5/00* | (2006.01) |
| *A61M 21/02* | (2006.01) |
| *A61B 5/055* | (2006.01) |
| *A61M 21/00* | (2006.01) |

(52) U.S. Cl.
CPC ............ *A61B 5/0046* (2013.01); *A61M 21/02* (2013.01); *A61B 5/055* (2013.01); *A61M 2021/005* (2013.01); *A61M 2021/0027* (2013.01); *A61M 2021/0044* (2013.01); *A61M 2205/505* (2013.01)

(58) Field of Classification Search
CPC . A61B 5/0046; A61M 21/00; A61M 21/0094; A61M 21/02; A61M 2021/0005; A61M 2021/0027; A61M 2021/0044; A61M 2021/005
See application file for complete search history.

(56) References Cited

U.S. PATENT DOCUMENTS 4,651,099 A * 3/1987 Vinegar ................. G01R 33/28
174/384
5,046,494 A * 9/1991 Searfoss ............... A61M 21/00
600/27

(Continued)

*Primary Examiner* — Carrie R Dorna
(74) *Attorney, Agent, or Firm* — Joseph S. Heino; Erin E. Kaprelian

(57) ABSTRACT

A method, system and software product are provided such that a patient in an MRI suite can select and enjoy personalized lighting, music, images and video with a touch screen for a program that is displayed on a system interactive digital unit or device. A wide and advanced variety of pre-programmed themes can be provided with the system, as is the option of creating customized content by the healthcare provider. Image panels help to "transport" the patient "away" from the confining space in the magnet bore of the MRI scanner, moving the patient's focus from the scanner to his or her surroundings. A ceiling image panel displays images of the patient's choice. Patients can also "dock" their own electronic device to enjoy their own audio visual content. The lighting of the suite can be returned to normal lighting when required and then back to the patient's original selections.

18 Claims, 3 Drawing Sheets

(56) References Cited

U.S. PATENT DOCUMENTS

| | | | |
|---|---|---|---|
| 6,544,165 B1* | 4/2003 | McNew | A61M 21/0094 600/27 |
| 6,870,673 B2* | 3/2005 | Cromer | A61M 21/02 353/119 |
| 7,773,777 B2 | 8/2010 | Raijmakers et al. | |
| 7,823,306 B1* | 11/2010 | Kersten | A61B 5/0046 40/436 |
| 2007/0121328 A1* | 5/2007 | Mondloch | F21V 3/04 362/294 |
| 2008/0303687 A1 | 12/2008 | Sempel et al. | |
| 2009/0080190 A1* | 3/2009 | Bauer | A61M 21/00 362/235 |
| 2010/0066911 A1 | 3/2010 | Grotenhuis et al. | |
| 2010/0238362 A1* | 9/2010 | Hughes | H04N 5/64 348/738 |

* cited by examiner

METHOD, SYSTEM AND SOFTWARE PRODUCT FOR CREATING VARIABLE ENVIRONMENTS IN MEDICAL DIAGNOSTIC IMAGING ROOMS

This Application claims the benefit of U.S. Provisional Application No. 61/616,194, filed Mar. 27, 2012.

FIELD OF THE INVENTION

This invention relates generally to art of controlling indoor human environments. It also relates generally to methods, systems and software products for acquiring, storing, processing, retrieving and displaying information and data. More specifically, it relates to a method, a system and a software product that allows a patient to control the environment of a medical diagnostic imaging room such that a more serene and calming environment is provided for the patient by using a pre-programmed scheme offered to the patient or, alternatively, by using the patient's interactive digital device. Doing so improves the patient's comfort, which also increases the efficiency and quality of the medical scan process as well as its results.

BACKGROUND OF THE INVENTION

In the experience of these inventors, many patients are prone to some elevated level of anxiety when undergoing any type of medical procedure or diagnostic testing. In the area of magnetic resonance imaging ("MRI") scans, in particular, those levels of anxiety are no less common. This is due in large part to the sense of confinement and, in serious instances, a claustrophobic response that is experienced by the patient when the patient is positioned within the bore of a typical MRI scanner and even between the upper and lower coils of a so-called "open" MRI scanner. An anxious patient will not have a positive experience during a typical MRI scan and may even cause the scan results to be compromised due to the patient's inability to relax. Current methods that attempt to induce a state of relaxation in patients have been to provide a light box or projected image in the scan room. However, such light boxes and projected images are intended to display only a static graphic or photographic image. In the view of these inventors, there is a need to provide patients who are about to undergo an MRI procedure with more than just a static photographic image to calm them.

Indeed, from the moment a patient enters an imaging suite, it is the inventors' intention that the patient be enveloped in a serene and calming environment to help minimize the patient's anxiety and to increase the patient's sense of control. It is necessary that such environmental control allow the patient to select personalized lighting, music, images and video to enjoy during the imaging process. It is further necessary to provide such patient-controlled modalities while also preventing electromagnetic ("EM") interference in the MRI suite which could compromise the quality of the MRI results.

SUMMARY OF THE INVENTION

In accordance with the foregoing, these inventors have provided a method and a system that provides a patient-centric care solution to the needs and goals identified above. Specifically, and in accordance with the present invention, a patient in an MRI suite can select and enjoy personalized lighting, music, images and video with a "tap" of the touch screen for a program that is displayed on a system interactive digital unit or device, such as an application residing within an iPad® (iPad is a registered mark of Apple, Inc.) application. An extremely wide and advanced variety of pre-programmed themes can be provided with the system, as is the option of creating additional customized content by the healthcare provider. Image panels help to "transport" the patient "away" from the confining space in the magnet bore of the MRI scanner in particular by moving the patient's focus from the scanner to his or her surroundings about the scanning room or suite. Specifically, a ceiling image panel in particular can display image slideshows or videos of the patient's choice. Patients can also "dock" their own iPhone® or iPod® (again, iPhone and iPod are registered marks of Apple, Inc.) to enjoy their own audio visual content in the ambient lighting of their choice. When necessary, another simple "tap" of the touch pad for the interactive digital device associated with the suite's iPad® application returns the suite to normal lighting that is conducive to necessary physician or technician procedures. Another "tap" and the suite environment returns to that which is set in accordance with the patient's original selections.

It should also be mentioned here that the method and system functionality of the present invention may be commercialized and marketed under the names MR Experience™, Experience Cassette™ and/or Caring MR Suite™ (MR Experience, Experience Cassette and Caring MR Suite are trademarks of PDC Facilities, Inc.). The foregoing and other features of the method, system and software product of the present invention will become apparent from the detailed description that follows.

DETAILED DESCRIPTION

As a prefatory statement, it is to be understood that the novel method and system of the present invention assumes usage of at least one computer program that is used in an electronic environment that comprises certain system building block "components." Those components are data structures, data processors and interfaces, and each component is a functional element. The data structures are places to organize and store data. The data processors are used to manipulate data by performing processes or applying algorithms to the data. The interfaces connect the data structures and the data processors to the outside world, including the virtual community that exists within the "world wide web" or "www," or to other data structures and data processors. The program includes source code which is a list of instructions, written in a selected computer language, and then converted into computer machine language, which language the computer uses to build the software "machine" described by the instructions. The software machine is made up of the components referred to above. The source code is a detailed "blueprint" telling the computer how to assemble those components into the software machine. Further, the source code is organized into separate files, files are organized into separate modules, and modules are organized into separate functions or routines to accomplish, via pre-programmed algorithms, the necessary steps in accordance with the method and system of the present invention. It is to be understood that the specific way that the source code is organized into files, modules and functions is a matter of programmer design choice and is not a limitation of the present invention.

As used herein, the MRI suite's interactive digital device is an iPad® device which enables one such application. The iPad® device is an interactive tablet computer having a platform for audio-visual media and, to the extent it is used with the method and system of the present invention, will be referred to in this detailed disclosure as the "system iPad® device." The system iPad® device functions on an operating system that is the same as that used for the iPod® device and the iPhone® device and is controlled by a multi-touch display panel, which is critical to the functionality of the method and system of the present invention.

Figure 1:
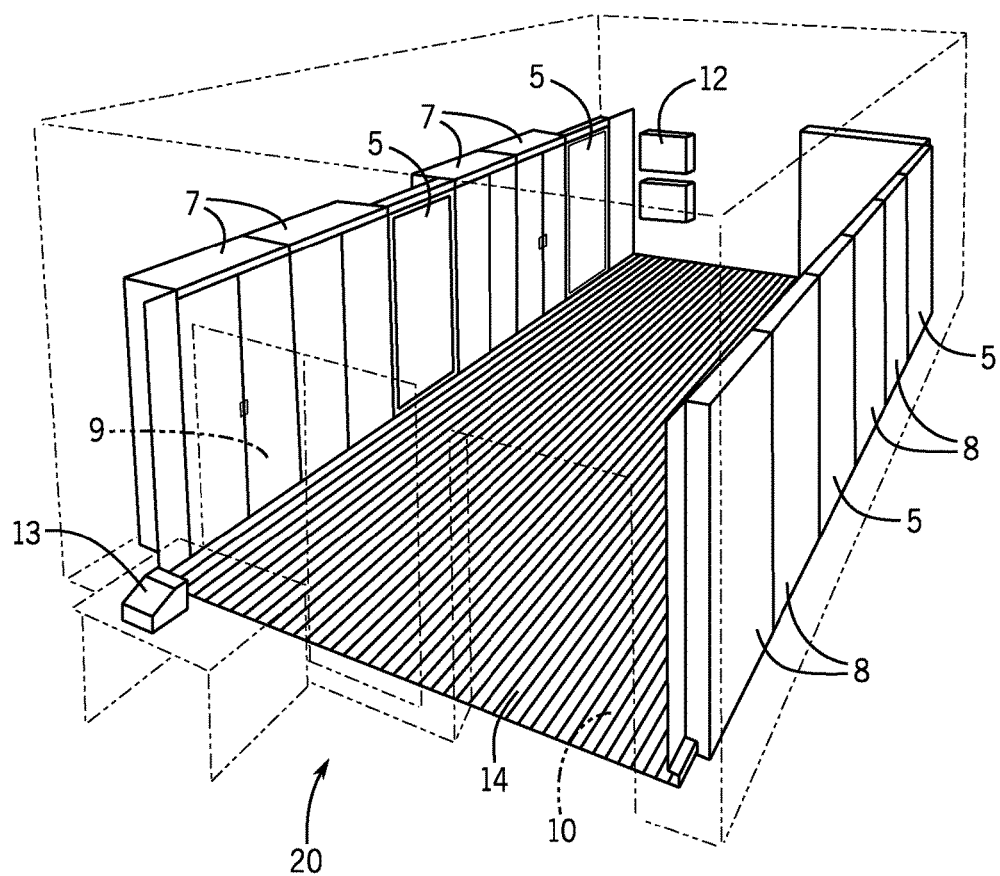
FIG. 1 is a perspective representation of one embodiment of an MRI scanning room, or "MRI suite," that has been modified to implement the system and method of the present invention.
Figure 3:
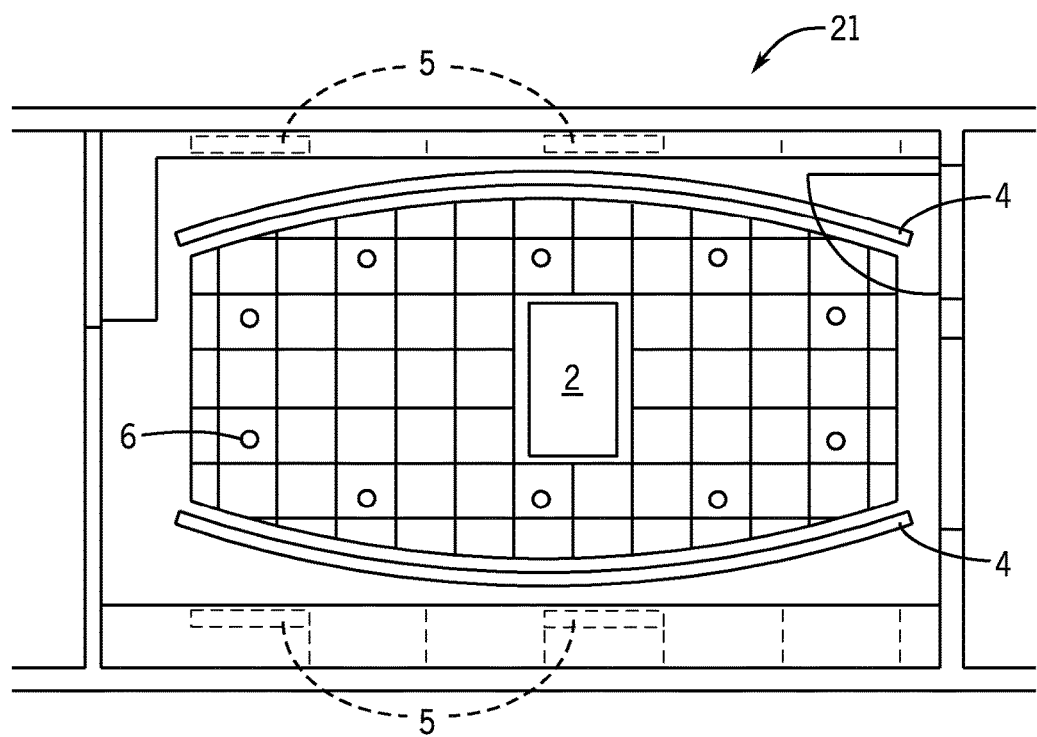
FIG. 3 is a top plan view of the ceiling of the room shown in FIG. 1.

Referring now to the detailed drawings, wherein like numbered elements represent like elements throughout, FIG. 1 shows the physical elements used in an MRI scan room, or MRI suite which is generally identified 20, that is configured in accordance with the present invention. As a preliminary matter, the method and system of the present invention is assumed to be implemented in an MRI suite 20 that physically comprises a room having an MRI scanner housed within it. The MRI scanner itself comprises a patient table that is used to support and move the patient relative to the bore of the MRI scanner. The MRI scanner itself is shown in phantom view in FIG. 3. The scan room 20 can assume any configuration and the precise location of the MRI scanner within the room 20 is not a limitation of the present invention.

The MRI suite 20, which is a radio frequency ("RF") enclosure, comprises a high STC acoustic tile ceiling 3, a floor 14, an RF window 9 and an RF door 10 as shown, the latter of which are intended to block EM or RF signals that could interfere with the functionality of the MRI scanner. The MRI suite 20, which is a radio frequency ("RF") enclosure, comprises a high performance sound transmission class ("STC") acoustic tile ceiling 3, a floor 14, an RF window 9 and an RF door 10 as shown, the latter of which are intended to block EM or RF signals that could interfere with the functionality of the MRI scanner. STC is a measure for rating the performance of a room surface as a barrier to airborne sound transmission, with a surface having an STC<35 considered low performance whereas one having an STC>55 is considered high performance.

In accordance with the present invention, however, the MRI suite further comprises an image panel 2 that is built into, mounted onto or suspended from the room ceiling 21 above the MRI scanner. The system of the present invention can also use a projection system or a high definition display monitor, similar to a liquid crystal display ("LCD") or light emitting diode ("LED") television with higher resolution to display digital images or video inside the MRI scan room 20. The system is engineered to function inside the RF enclosure without emitting EM or RF signals that could interfere with the functionality of the MRI scanner.

Figure 2:
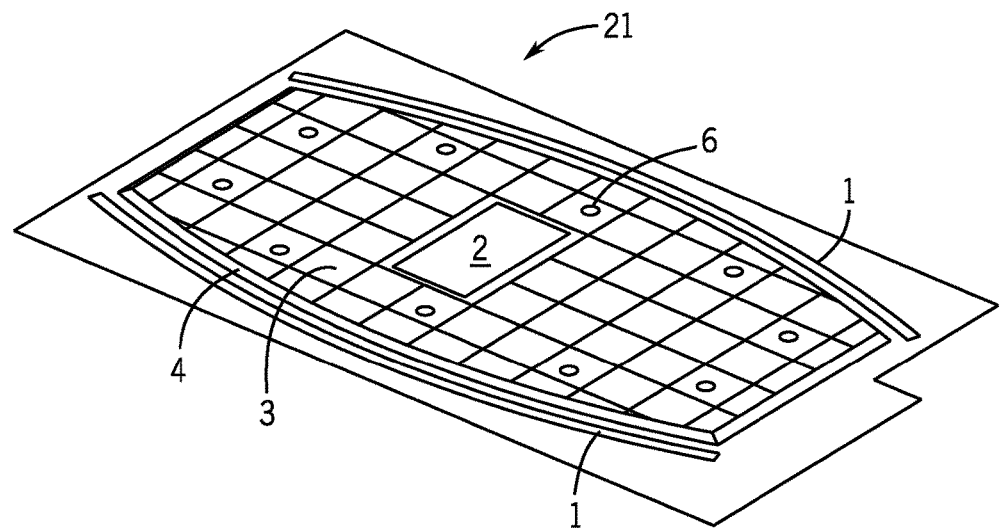
FIG. 2 is a top perspective view of the ceiling of the room shown in FIG. 1.

LED lighting, both white and color changing, is also included within the suite ceiling 21 in the illustrated embodiment. See also FIGS. 2 and 3. In the embodiment shown, that lighting comprises opposing curved color changing LED light coves 1 disposed in proximity to a curved soffit 4 and LED can lights 6, the can lights 6 being dimmable white lights. It is to be understood that the light coves 1 could be straight, or in-line, or assume some other configuration with the same intended effectiveness and without deviating from the scope of the present invention. All lighting in the MRI scan room 20 is low voltage direct current ("DC") lighting, including the white lights that are used during physician and technician-involved phases of the scan. Further, a number of vertical LED color changing wall light boxes 5 are provided. It is also to be understood that the quantity of lights in the scan room 20 can be changed for different size scan rooms 20. Disposed between the wall light boxes 5 are wall storage cabinets 7 and false front cabinets 8, as desired or required. One or more electronics cabinets 12 are also provided. An iPad® control box 13 is situated in a control room which is just outside the scan room 20.

Figure 4:
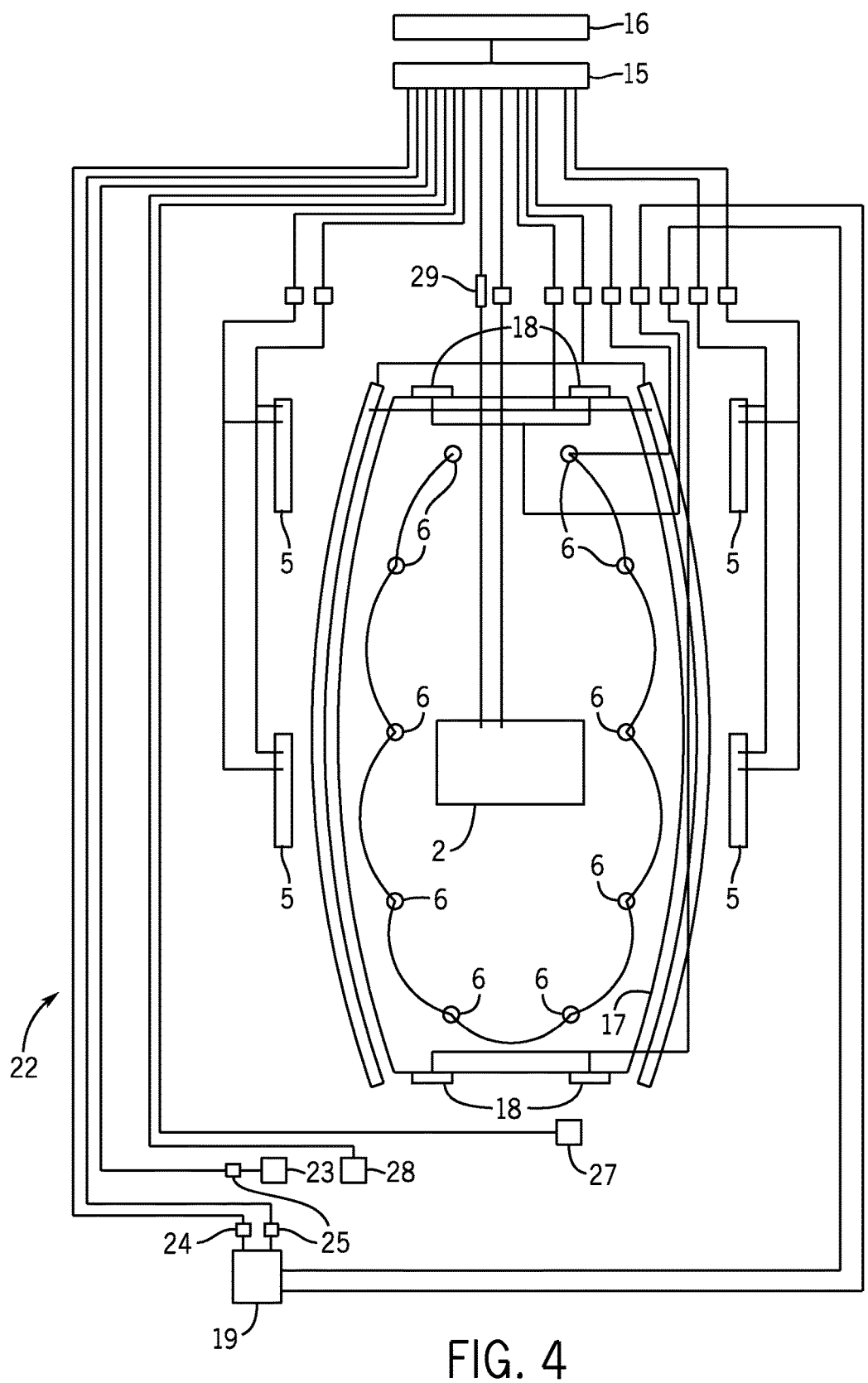
FIG. 4 is an electrical schematic and plan view for the room shown in FIG. 1.

As shown in the electrical schematic, generally identified 22, in FIG. 4, a first system control box 15 and a second system control box 16 supply the room lighting and provide a "theme" control. That is, the control boxes 15, 16 generally comprise a DC lighting controller, DC power distribution, theme computer, video control and sound control. The control boxes 15, 16 require electrical service connections and all DC cabling from the boxes to multiple components including, by way of example, the ceiling mounted HD monitor 2 and fiber optic pass-through 14; the curved LED color changing ceiling light coves 1, 3; speakers 18; the vertical LED color changing light panels 5; the LED can lights 6; and a plurality of EMI filters 26 to such components. Outside of the MRI scan room 20, which would be the control area or control room, similar connections are made to a stereo receiver 19; an iPad® control dock 23; an HDMI extender receiver 24; an HDMI extender sender 25; an iPad® control dock 27 for the patient; and an iPad® control dock 28 for the technologist. The entire suite 20 is controlled by the remote system iPad® device control docks which are located in the control room.

The control system comes with a plurality of pre-programmed "themes" and the ability to include survey questions that the patient will answer before and after the scan. Answers to the survey questions will assist the healthcare provider to comply with governmental patient satisfaction requirements. Custom themes, content and survey questions can be developed and implemented by the system user as well. The system includes a secondary control panel for the MRI technologist to over-ride the theme and control lighting when desired or required. Additionally, docks for iPhone® and iPod® devices will allow the patient to dock his or her own personal devices as well. This allows the patient to listen to and watch personal content during the scan. Two iPads® devices and one secondary control for the MRI technologist station are preferably included as well.

As alluded to above, the themes, or content, provide a variety of topics that are specifically developed to provide a distraction for younger patients and the feeling of control and personal choice for all patients. For example, for patients who prefer a soft lit white room free of music and image display, a "white room" theme with dimming capability is provided as a theme.

In application, the operation of the method and system of the present invention is initiated, from the patient's perspective, prior to entering the MRI scan room 20. When the patient is brought to the scan room 20, and before entering it, he or she will select the experience the patient wants. The control dock 27 for the patient's iPad® device can be located at the MRI room entry door 10 or operate in wireless mode anywhere within the control room or preparation room. From that device, the patient will select one of ten or so preprogrammed themes. The patient may also select a custom theme wherein the color selection is made by means of a color wheel showing all available colors, a music playlist and a visual selection, which could be a video or a picture slideshow format.

If the patient has his or her own iPod®, iPhone® or iPad® device, the patient may select his or her own music playlist. The patient may also select his or her own video or picture slideshow from the same devices if they have one available. The patient can also select to have the audio and video/slideshow using a variety of programs, one such being AirPlay® (AirPlay is a registered mark of Apple, Inc.) wireless streaming of audio and visual data. From the system iPad® device, the patient would select a custom theme and select a color via a color wheel with all available colors. The patient would also select a visual selection, which would be a video or picture slideshow.

If the patient has his or her own iPad® or iPad Mini™, the patient could similarly select their own music playlist and plug into the jack at the technologist control panel in the control room. From the system iPad® device, the patient would select a custom theme and select a color via a color wheel with all of the available colors. The patient would also select a visual selection, which would be a video or picture slideshow shown on the image panel 2. The MRI technologist will have ultimate control of the dimming of the lights 1, 5, 6, however. There will be up to seven different dimming zones, including color LEDs, white LEDs and can lights 6 (up to five zones). Once the MRI scan has been initiated, the technologist will be able to press a "Lights On" button on the system iPad® device should he or she need to turn the lights 1,5,6 on full brightness.

In accordance with the foregoing, it will be seen that there has been provided a new and useful method and system that provides a patient-centric care solution whereby a patient in an MRI suite can select and enjoy personalized lighting, music, images and video with a "tap" of the system's iPad®. A wide variety of pre-programmed themes can be provided with the system, as is the option of creating additional customized content by the healthcare provider. Image panels help to "transport" the patient away from the confining space in the magnet bore of the MRI scanner in particular. A ceiling image panel in particular can display image slideshows or videos of the patient's choice. Patients can also "dock" their own iPhone® or iPod® devices to enjoy their personalized audio visual content in the ambient lighting of their choice. When necessary, another simple "tap" of the suite's system iPad® device returns the suite to normal lighting that is conducive to necessary physician or technician procedures. Another "tap" and the suite environment returns to that which is set in accordance with the patient's original selections. Further, the system of the present invention is engineered to function inside the RF enclosure without emitting EM or RF signals that could interfere with the MRI procedure.

The details of the invention having been disclosed in accordance with the foregoing, we claim:

1. A system for creating variable environments for a patient in a radio frequency (RF) room, the system comprising:
   at least one low voltage direct current (DC) white light;
   at least one low voltage DC color-changing light;
   a visual display, wherein the visual display comprises an image panel suspended from a ceiling of the RF room; and
   a theme controller coupled to the at least one DC white light, the at least one DC color-changing light, and the visual display, wherein the theme controller further comprises:
      a DC lighting controller;
      a DC power distribution;
      a theme computer to control a plurality of pre-programmed themes, wherein each theme of the plurality of themes comprises:
         a light color of the at least one low-voltage DC color-changing light;
         an audio selection; and
         a visual selection;
      a video controller to control the visual selection; and
      an audio controller to control the audio selection;
   wherein the RF room blocks electromagnetic and radio frequency signals that interfere with a functionality of a Magnetic Resonance Imaging (MRI) scanner disposed within the RF room.

2. The system of claim 1, wherein:
   the RF room comprises the MRI scanner; and
   the RF room is a medical diagnostic imaging room of the type that prevents electromagnetic interference with the MRI scanner, wherein the imaging room further comprises:
      a ceiling including the at least one white light;
      an RF window to block electromagnetic and radio frequency signals; and
      an RF door to block electromagnetic and radio frequency signals;
   the at least one color-changing light comprises a pair of color-changing LED light alcoves disposed above the scanner;
   the visual display is adapted to be in view of the patient; and
   the at least one color-changing light further comprises a plurality of wall light boxes.

3. The system of claim 2, wherein the theme controller is coupled to a personal computing device such that an output from the personal computing device controls the theme controller.

4. The system of claim 2, wherein the theme controller is controlled by use of a system interactive digital device.

5. The system of claim 2, wherein the theme controller is coupled to an interactive personal digital unit such that an output of the interactive personal digital unit controls the theme controller.

6. The system of claim 2, wherein the system further comprises at least one audio speaker.

7. The system of claim 1, wherein the visual display comprises the image panel mounted onto a ceiling of the RF room.

8. The system of claim 1, wherein the visual display comprises the image panel built into a ceiling of the RF room.

9. A method for creating variable environments for a patient in a radio frequency (RF) enclosure:
   receiving, at a control system, a plurality of inputs comprising a plurality of answers to a plurality of survey questions;
   determining a theme based on the plurality of inputs, wherein the theme includes:
      a light color;
      an audio selection; and
      a visual selection, the visual selection comprising a video or a picture slideshow;

transmitting the determined theme to a theme controller, wherein the theme controller is coupled to:
- at least one low voltage direct current (DC) white light;
- at least one low voltage DC color-changing light;
- a visual display, wherein the visual display comprises an image panel suspended from a ceiling of the RF room;
- a theme computer;
- a docking station; and
- an audio controller;

changing, by the theme controller, the brightness of the at least one white light, the color of the at least one color-changing light, and the visual content of the visual display based on the determined theme transmitted to the theme controller.

10. The method of claim 9, further comprising:
docking a personal computing device at the docking station such that the personal computing device is coupled to the theme controller; and
receiving an output from the personal computing device at the theme controller, wherein the output from the personal computing device determines the theme.

11. The method of claim 9, further comprising:
docking a system interactive digital device at the docking station such that the system interactive digital device is coupled to the theme controller; and
receiving an output from the system interactive digital device at the theme controller, wherein the output from the system interactive digital device determines the theme.

12. The method of claim 9, further comprising:
docking an interactive personal digital unit at the docking station such that the interactive personal digital unit is coupled to the theme controller; and
receiving an output from the interactive personal digital unit at the theme controller, wherein the output from the interactive personal digital unit determines the theme.

13. The method of claim 9 wherein:
the RF enclosure comprises an imaging room, further comprising:
- an RF window;
- an RF door;

all lighting comprises low voltage direct current lighting;
the at least one white light is disposed within a ceiling of the imaging room;
the at least one color-changing light comprises a pair of color-changing LED light alcoves disposed above a Magnetic Resonance Imaging (MRI) scanner;
the visual display is adapted to be in view of the patient; and
the at least one color-changing light further comprises a plurality of wall light boxes.

14. The method of claim 13, further comprising providing an audio speaker, wherein the audio speaker is coupled to the theme controller.

15. The method of claim 9, further comprising interrupting the determined theme to normal lighting for patient inspection.

16. The method of claim 15, further comprising returning to the determined theme after the normal lighting interruption.

17. The method of claim 9, wherein the visual display comprises the image panel mounted onto a ceiling of the RF room.

18. The method of claim 9, wherein the visual display comprises the image panel built into a ceiling of the RF room.

* * * * *